United States Patent [19]

D'Costa

[11] Patent Number: 5,525,511

[45] Date of Patent: Jun. 11, 1996

[54] ELECTROCHEMICAL BIOSENSOR STABILITY

[75] Inventor: Eric D'Costa, Newport Pagnell, England

[73] Assignee: Environmental & Medical Products Ltd., London, England

[21] Appl. No.: 50,197

[22] PCT Filed: Aug. 28, 1991

[86] PCT No.: PCT/GB91/01444

§ 371 Date: Apr. 28, 1993

§ 102(e) Date: Apr. 28, 1993

[87] PCT Pub. No.: WO92/04466

PCT Pub. Date: Mar. 19, 1992

[30] Foreign Application Priority Data

Sep. 1, 1990 [GB] United Kingdom ............ 9019126

[51] Int. Cl.⁶ ............................................ C12M 1/40
[52] U.S. Cl. ............... 435/287.9; 435/817; 435/287.7; 204/403
[58] Field of Search ................................ 435/4, 12, 14, 435/288, 291, 817; 204/153.12, 153.17, 403, 415

[56] References Cited

U.S. PATENT DOCUMENTS 3,838,033  9/1974  Mindt et al. ........................... 204/403
4,820,399  4/1989  Senda et al. ........................... 204/403

FOREIGN PATENT DOCUMENTS 0234938   9/1987  European Pat. Off. .
0390390  10/1990  European Pat. Off. .
0415124   3/1991  European Pat. Off. .
2240849  10/1987  Japan ..................................... 204/403
2099850   4/1990  Japan ..................................... 204/403

OTHER PUBLICATIONS

Patent Abstracts of Japan. vol. 14, No. 309(p.–1071) (4252) Jul. 4, 1990.

Mizutani et al. "Ferrocene–Mediated Enzyme Electrode . . ." Bull. Chem. Soc. Japan vol. 61, No. 12 (1988) pp. 4458–4460.

Pickup et al. "Potentially–Implantable, Amperometric Glucose Sensors . . ." Biosensors, vol. 4 (1989) pp. 109–119.

Primary Examiner—William H. Beisner
Attorney, Agent, or Firm—Merchant. Gould, Smith, Edell, Welter & Schmidt

[57] ABSTRACT

An electrochemical biosensor comprising a conductive support member (2) mounted on a substrate (1) and carbon pads (4) overlying the conductors (2) and surmounted by working electrode and reference electrode pads (5) and (6). A membrane (8) applied over the electrodes incorporates a quantity of mediator to facilitate repeated use of the biosensor.

9 Claims, 12 Drawing Sheets

ELECTROCHEMICAL BIOSENSOR STABILITY

FIELD OF THE INVENTION

This invention relates to an electrochemical biosensor of the kind wherein an enzyme-containing reagent system is applied to an electrically conductive support member and which responds amperometrically to the catalytic activity of the enzyme in the presence of its substrate.

BACKGROUND OF THE INVENTION

Immobilisation of an enzyme upon an electrode impedes conduction of electrons between the active site of the enzyme and the electrode. Electron carriers or mediators have been employed to overcome this disadvantage and to enhance the reliability and sensitivity of the electron transfer.

Mediator assisted biosensors do not give consistent results upon repeated use, especially those made by screen printing methods. Commercial products are designed for use once or twice only, after which they must be discarded.

SUMMARY OF THE INVENTION

According to a first aspect of the present invention an electrochemical biosensor comprises:

a conductive support member;

an enzyme system including a mediator immobilised on the support member; and a covering membrane, characterised in that the membrane incorporates a quantity of a mediator.

The mediator contained in the membrane may be the same or different to that of the enzyme system. Preferably the mediators are the same.

According to a second aspect of the present invention an electrical biosensor comprises:

a conductive support member;

an enzyme system incorporating a mediator immobilised on the support member; and a conductive membrane;

characterised in that the biosensor provides a substantially quantitative and amperometric response when used for 50 repeat tests with an analyte.

We have found surprisingly that provision of a quantity of mediator within the membrane provides a biosensor which may be used repeatedly, for example preferred biosensors may be used 1000 times or more, without significant reduction in the quantitative and amperometric response. Biosensors in accordance with this invention may be incorporated into automatic analytical equipment for example for monitoring analytes in a sample stream, or implantation to allow in vivo metabolic analysis. Further applications include blood analysis for example for glucose, lactate, creatinine, urea, pyruvate etc. The invention may also be used for process control for industrial fermentation and brewing, amino acid production and for food processing, for example for monitoring glucose levels in meat. Monitoring of mammilarian cell cultures is also facilitated.

Membranes which may be applied to the enzyme containing layer of the biosensor act as a diffusion barrier, preventing loss of the components of the enzyme containing layer.

The membrane may be composed of various materials. Preferred materials include ethyl hydroxyethyl cellulose, ethyl cellulose, cellulose acetate, polyvinylchloride, polyurethane, polycarbonate, cellulose nitrate, polyurethane, cellulose acetate, aryl polyethers for example polyether sulphone or polyether ketone including functionalised polyaryl ethers, such as sulphonated polyether sulphonate.

Anionic or cationic ion exchange membrane materials may be used. For example Nafion membranes may be used to retain the mediator in the charged state.

In most applications non-ionic membranes are preferred.

Membrane thickness of 0.1 to 100 microns may be used.

In preferred embodiments of the invention wherein the enzyme system is partially soluble in aqueous solvents, the membrane and mediator are preferably soluble in a non aqueous solvent. This prevents leaching of the enzyme reagents during casting of the membrane. It also prevents solubilisation of the printed electrode matrix. The solvents for the membrane and mediator may be a mixture of two or more solvents, one of which may be a good solvent for the mediator and another being a good solvent for the membrane material, the volatilities of the solvents being selected so that the concentration of the mediator across the membrane may be selectively controlled.

The concentration of the mediator in the membrane may be up to 50 mg.g$^{-1}$, preferably 5 to 20 mg.g$^{-1}$ for example 10 mg.g$^{-1}$.

The mediators which may be employed may be selected from several classes i. Heterofulvalene Pi-donors for example tetrathiafulvalene and tetraselenafulvalene.

ii. Metallocenes for example ferrocene, nickelocene and selenocene.

iii. Quinones for example benzoquinone.

iv. Metal complexes based on platinum group metals or transition group elements and organic ligands: for example platinates, ruthenates and tungstates.

v. Organic metal complexes for example TCNQ complexes. TCNQ derivatives and NMP$^+$NCNQ$^-$ and TTF$^+$ TCNQ$^-$-type charge transfer complexes.

The enzyme containing layer may comprise conductive carbon particles coated with the enzyme, mediator and a binder. The binder may be chemically similar to the membrane material. For example a hydroxyethyl cellulose binder may be used in conjunction with an ethyl hydroxyethyl cellulose membrane material. This affords compatibility between the enzyme layer and the membrane and good adhesion.

A thin layer of non-mediator membrane material (EHEC) may be cast over the electrode before the mediator-containing membrane. This provides good adhesion but prevents excess mediator leaching from the membrane into the electrode. Covering membranes may also be required to confer biocompatibility, antifouling or diffusion properties needed to suit the application.

Membranes may be applied by spin or dip coating or by ink jet printing. Ink jet printing has the advantage that the mediator-doped membrane is only applied to selected regions of the substrate. The mediator may also be included in precast membranes which are subsequently applied to the electrode. Such precast membranes may comprise cellulose nitrate, cellulose acetate polycarbonate, polyamide or other commercially used membrane materials. Precast membranes may be secured to the electrode by conventional methods, eg by adhesive or using physical attachments.

BRIEF DESCRIPTION OF THE DRAWINGS

The invention is further described by means of example but not in any limitative sense, with reference to the accompanying drawings of which.

DESCRIPTION OF THE PREFERRED EMBODIMENT

Graphite powder grade $T_{10}$ was obtained from Morganite Electrical Carbon Ltd. Swansea, Wales. Micronised silver chloride was obtained from MCA Services, Cambridge, England. Polyvinylchloride substrate (0.650 mm thick) was obtained from Mazzucchelli Limited, Wallington, England. Silver (Electrodag 477 SS RF) and carbon (Electrodag 423 SS) inks were purchased from Acheson Colloids Co, Plymouth, England. Hydroxyethyl cellulose, ethylene glycol and diethyleneglycol monoethyl ether acetate were obtained from Fluka Chemicals Limited, Glossop, England. Ethyl hydroxy ethyl cellulose (high viscosity grade) was purchased from Polysciences, Inc. Warrington, U.S.A. All other chemicals were of reagent grade.

1. The working electrode (WE) ink was prepared as follows:

(i) Weight 133.6 mg TTF (Aldrich) in to a glass universal bottle (in 30 ml capacity) and add approximately 5 ml diethyl ether (Fluka).

(ii) Weigh 2 g $T_{10}$ graphite (Morganite) into a large, high-sided glass petri dish.

(iii) Add the TTF dissolved in diethyl ether to the graphite. Wash out any remaining TTF from the universal bottle with approximately 4 ml diethyl ether and add the washings to the graphite.

(iv) In a fume hood, mix the TTF and graphite using a spatula until all the diethyl ether has evaporated and the TTF is deposited on to the graphite.

(v) Weight 536 mg GOD (Glucox-PS:Sturge) into a straight-sided, wide-necked screw top jar (100 ml capacity). Add 4.67 g of a two percent (w/v)) aqueous solution of hydroxy ethyl cellulose (HEC) (Fluka) containing six percent (w/w) ethylene glycol (Fluka) and mix to dissolve the GOD.

(vi) Mix the graphite/TTF into the GOD solution and rotate on an angled (45°) rotary mixer at 4 rpm for two to three hours at room temperature.

NB a For dimethyl ferrocene (DMF) the above precedure was repeated but DMF was substituted weight-for-weight for TTF.

b For tetracyanoquinodimethane (TCNQ) the above procedure was repeated but substituting TCNQ for TTF in a weight-for-weight manner. In addition, the TCNQ was dissolved in 200 ml toluene (rather than in diethyl ether for step (iii) above). In this case, the TCNQ/toulene washings (approximately 20 ml) were also added to the $T_{10}$ graphite powder 2. The reference electrode (RE) ink was prepared as follows:

Micronised silver chloride was added to silver ink to a content of thirty five percent (w/w) and mixed thoroughly. The mixture was thinned to a printable consistency by the addition of nine percent (w/w) diethyleneglycol monoethyl ether acetate.

3. The silver, carbon and insulating inks were used as received.

Figure 9:
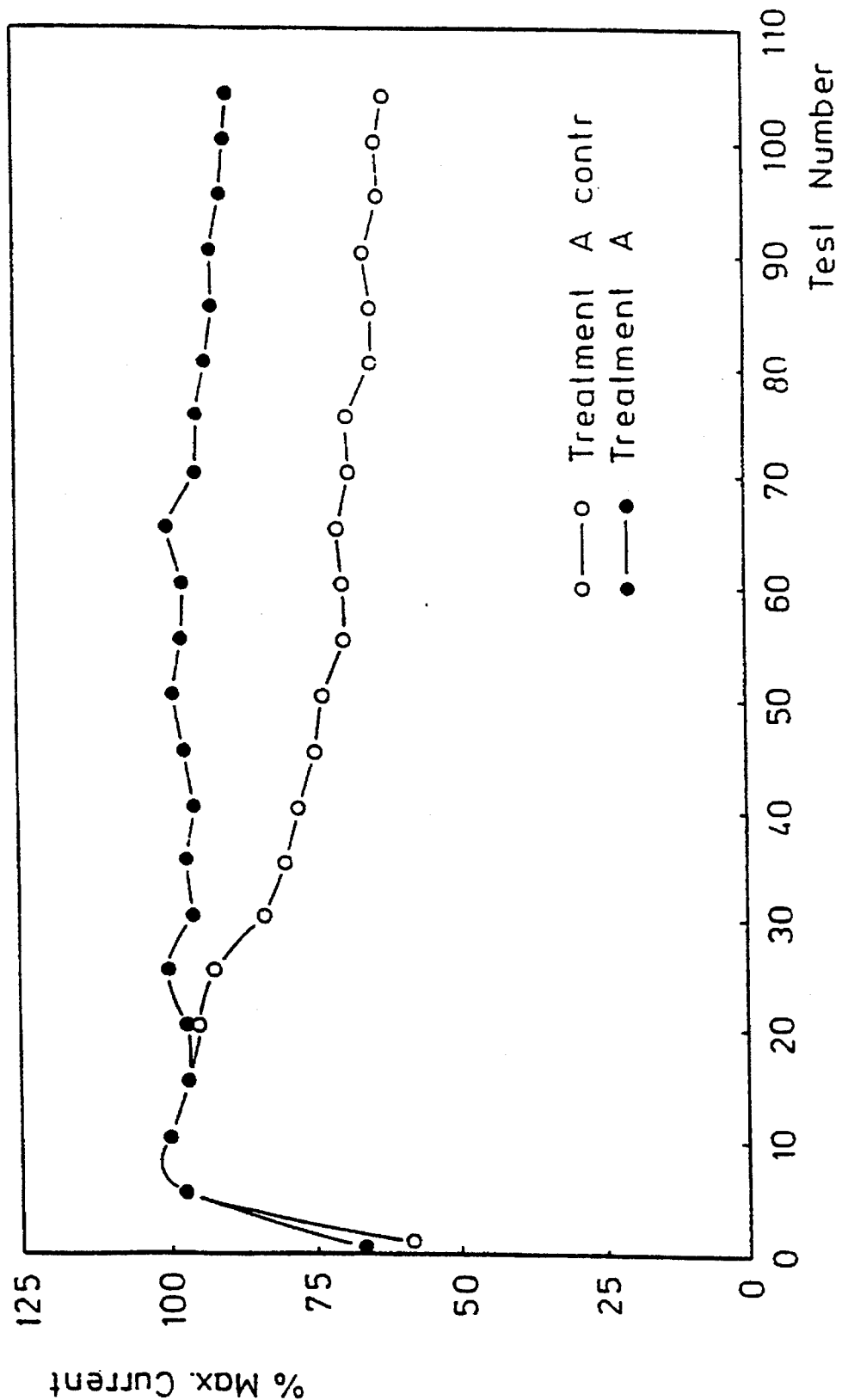
Figure 10:
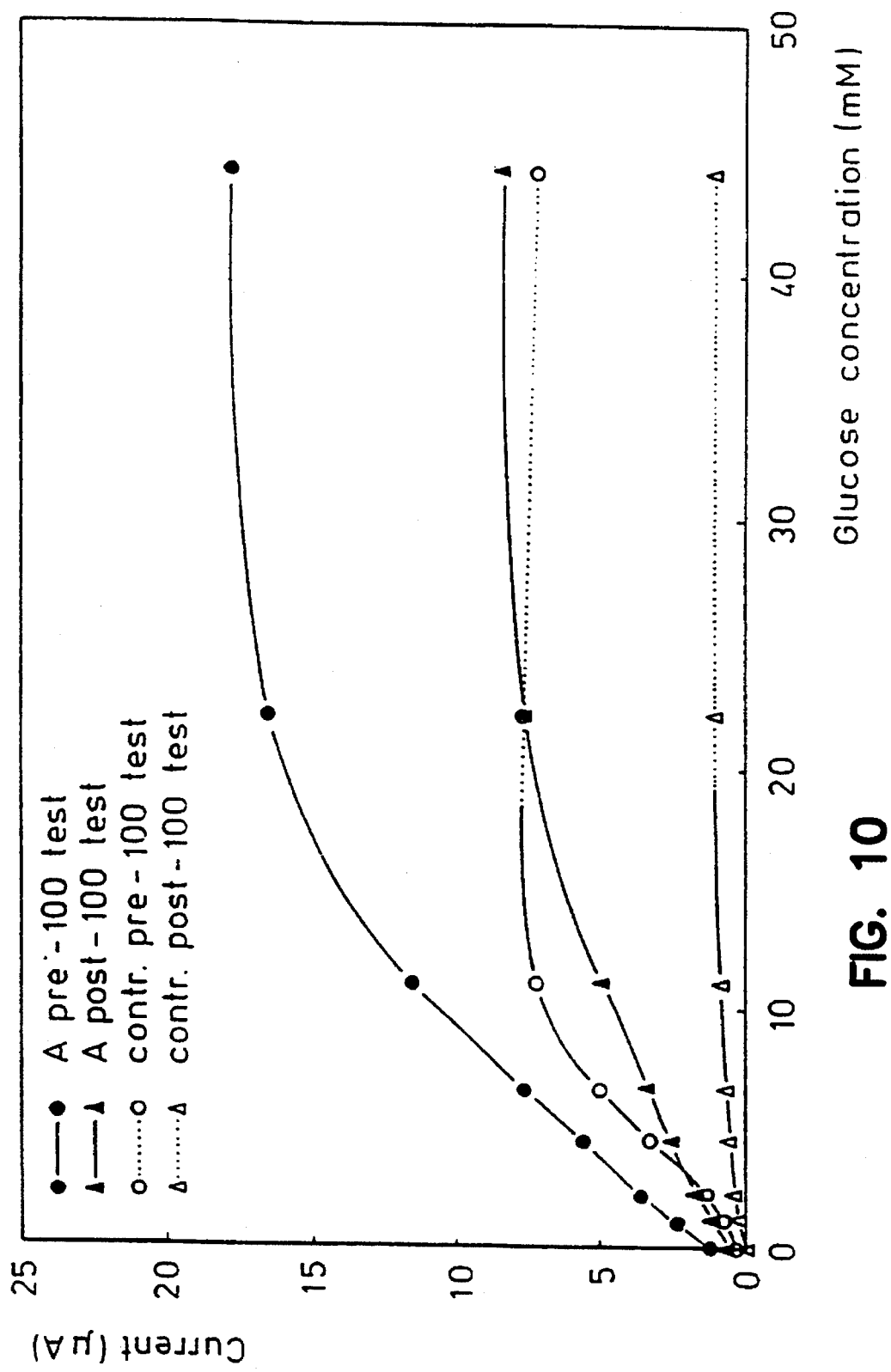

The sensor consisted of a PVC substrate (0.65 mm thick) upon which was printed a series of layers (see FIG. 9). All layers were printed through polyester screens using a Model 245 screen printer (DEK Printing Machines Ltd. Weymouth, England). Electrical contact to the WE and RE pads was provided by silver tracks. A carbon layer was positioned over the conductive tracks ensuring that the silver did not make contact with the analyte solution. The WE and RE pads were positioned over the carbon layers. An insulating layer, with openings allowing external electrical contact to one end of the strip and analyte access to the WE and RE at the other, was printed over the whole strip. Four such sensors were printed on each substrate.

An electrochemical interface under IBM-compatible computer control was used to measure simultaneously the current from four strip sensors supported in a thermostatically controlled glass cell containing 20 ml quiescent test solution. A potential of 200 mV vs Ag/AgCl (printed) reference electrode was applied to the working electrode and the current was measured after thirty seconds.

EXAMPLE 1

Standard TTF/GOD printed electrodes (HEC binder: see experimental procedures) were modified by spin-coating with a 6% (w/w) solution of EHEC (ethylhydroxyethyl cellulose) in toluene containing 10 mg g$^{-1}$ TTF. The spin-coating was carried out at approx 1000 rpm for two to five seconds. The membrane coated electrodes were dried rapidly (two to five seconds) in a stream of air.

Repeat tests were carried out in 11 mM glucose in 20 mM sodium phosphate (pH 7.4) containing 0.1M KCl at 25° C. The tests were for thirty seconds duration at a potential of +200 mV v. Ag/AgCl (printed).

Figure 1:
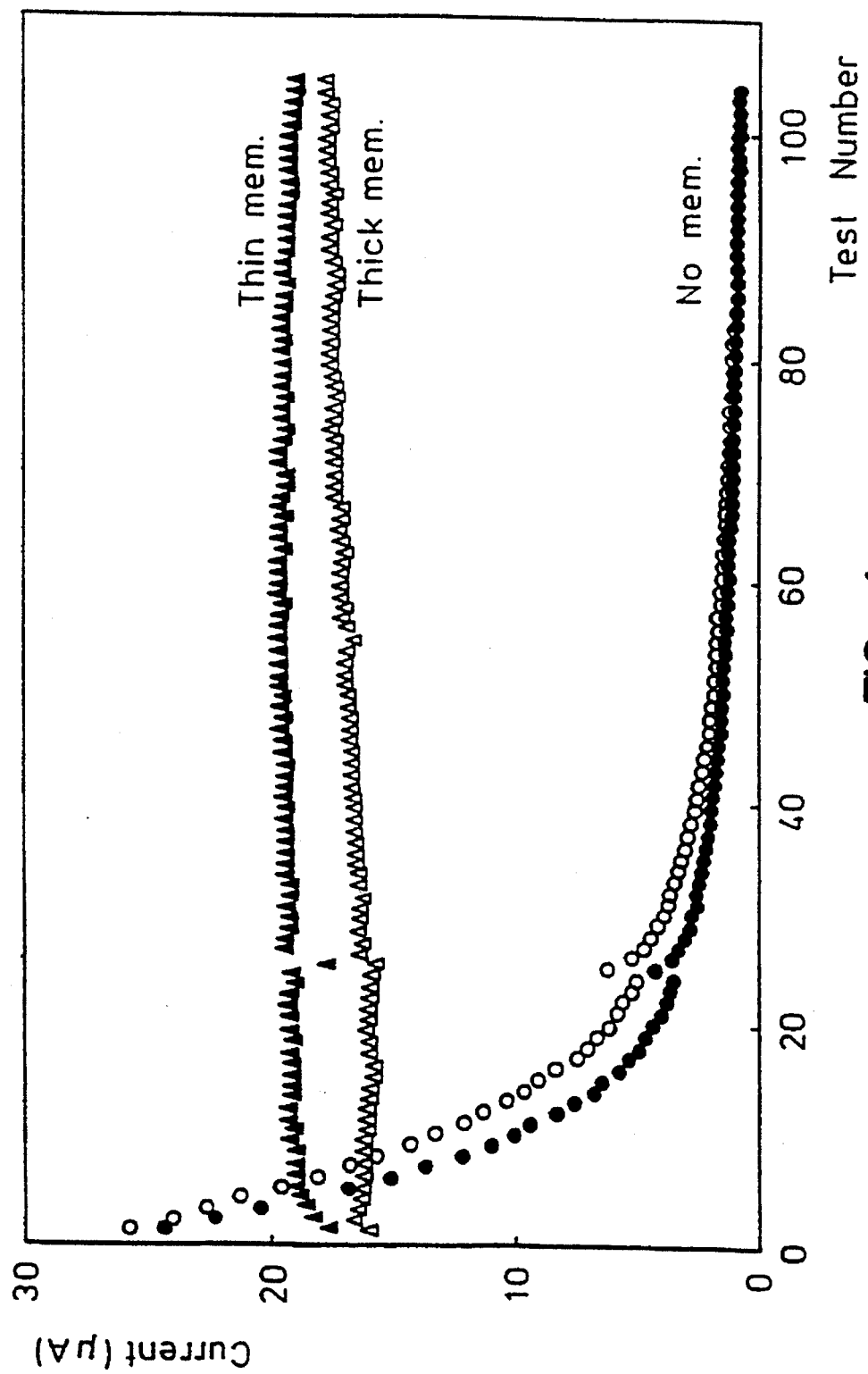
FIG. 1 illustrates repeated test of a TTF membrane covered TTF/GOD electrod in accordance with this invention in 11 mM glucose.

No significant loss in activity of the coated electrodes was observed after 100 assays. The untreated electrodes, however, lost approximately ninety per cent activity by the fiftieth assay. The results are illustrated in FIG. 1.

Figure 2:
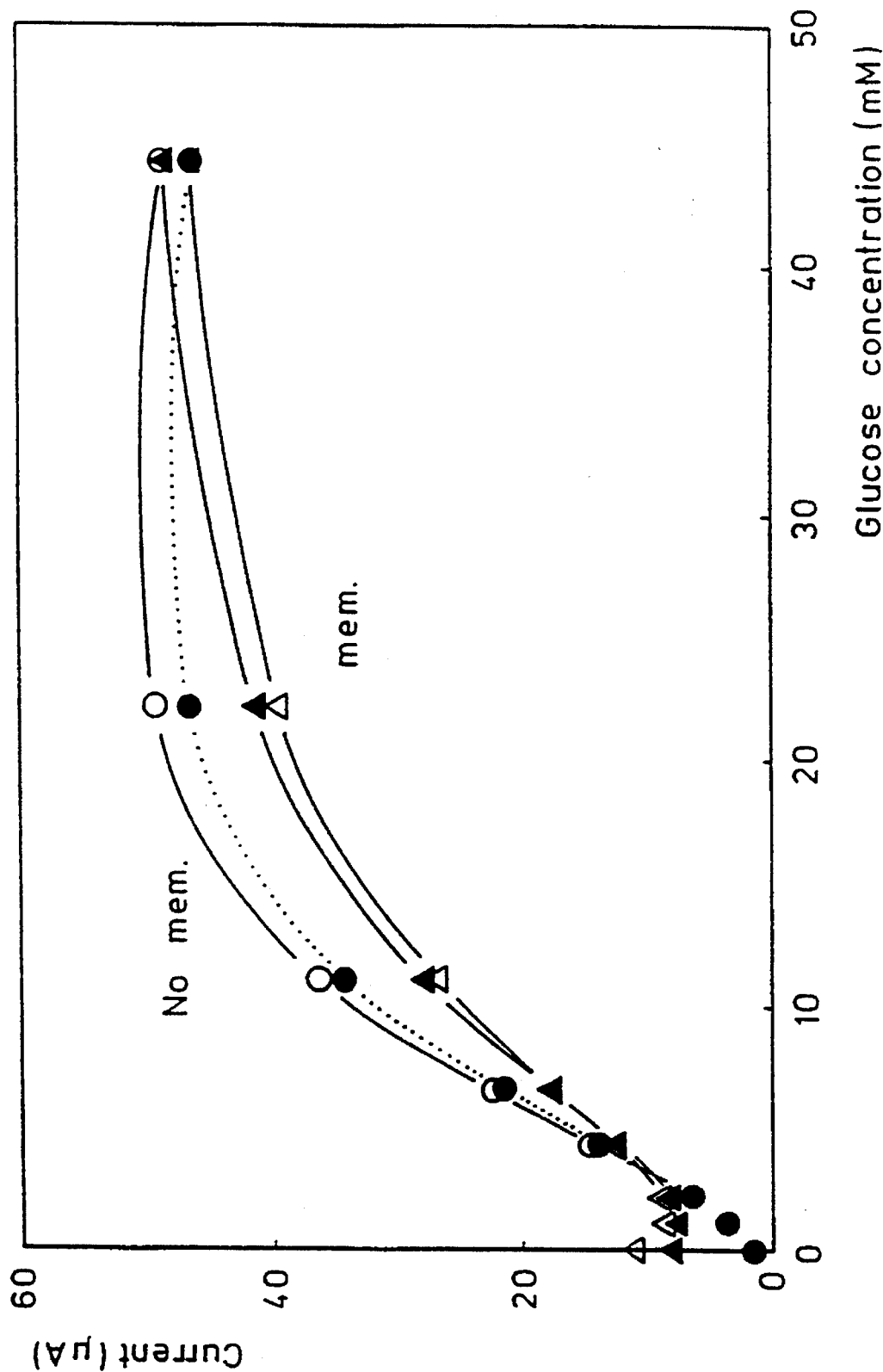
FIG. 2 illustrates calibration of TTF membrane covered and free printed TTF/GOD electrodes.

The calibration curve between zero and 44.41 mM glucose had a higher background than the untreated electrodes and little change in signal could be observed between zero and 2.22 mM glucose. This may have been due to the high TTF concentration or it may be due to the requirement for some degree of pre-treatment. The coated electrodes showed increasing responses between 22.2 and 44.41 mM glucose, whereas the untreated electrodes did not. This flattening of the calibration curve was thought to be due to diffusion limitation to glucose; an expected result (FIG. 2).

Figure 3:
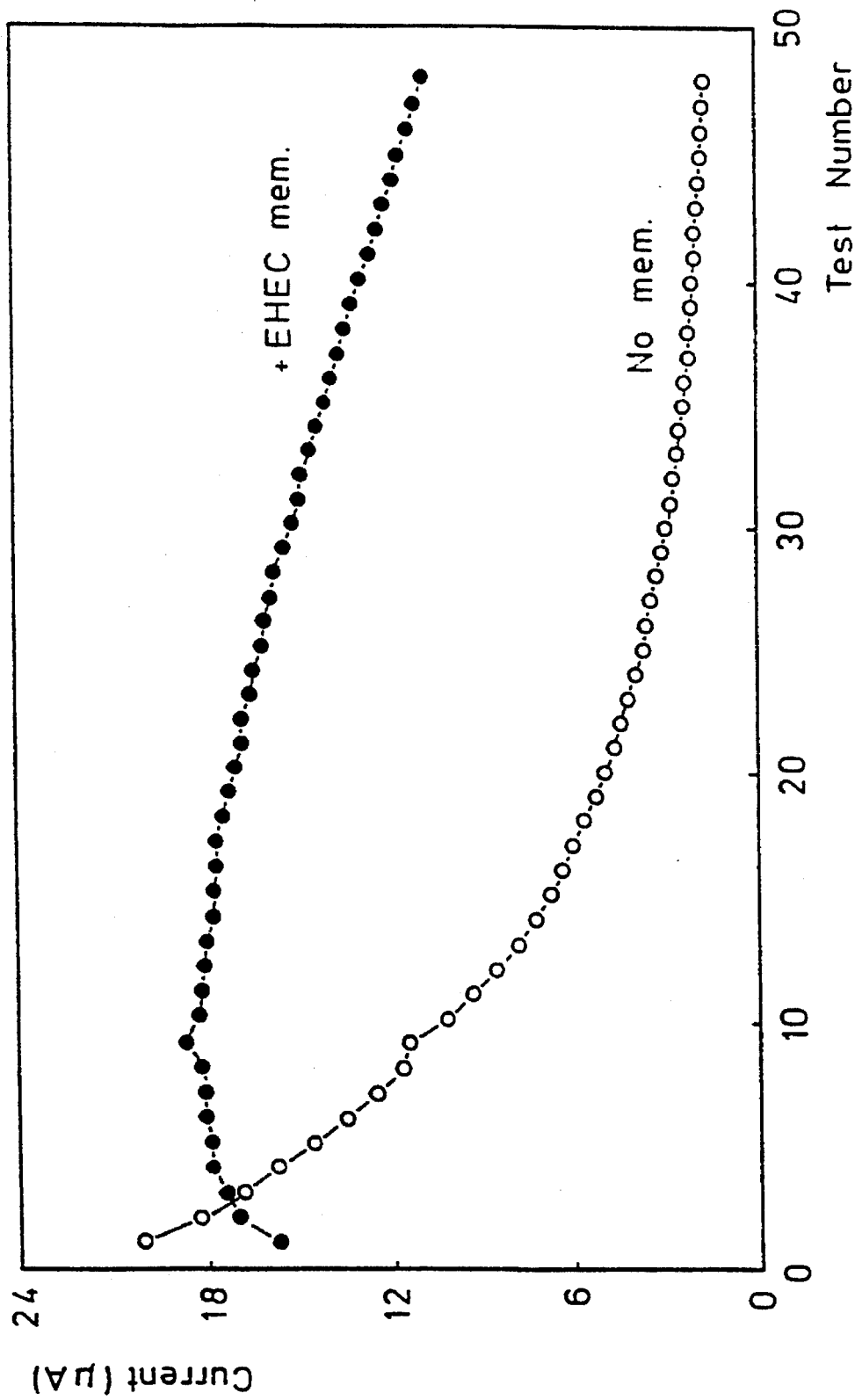
FIG. 3 illustrates repeated test of mediator free membrane covered TTF/GOD electrodes in 11 mM glucose.
Figure 4:
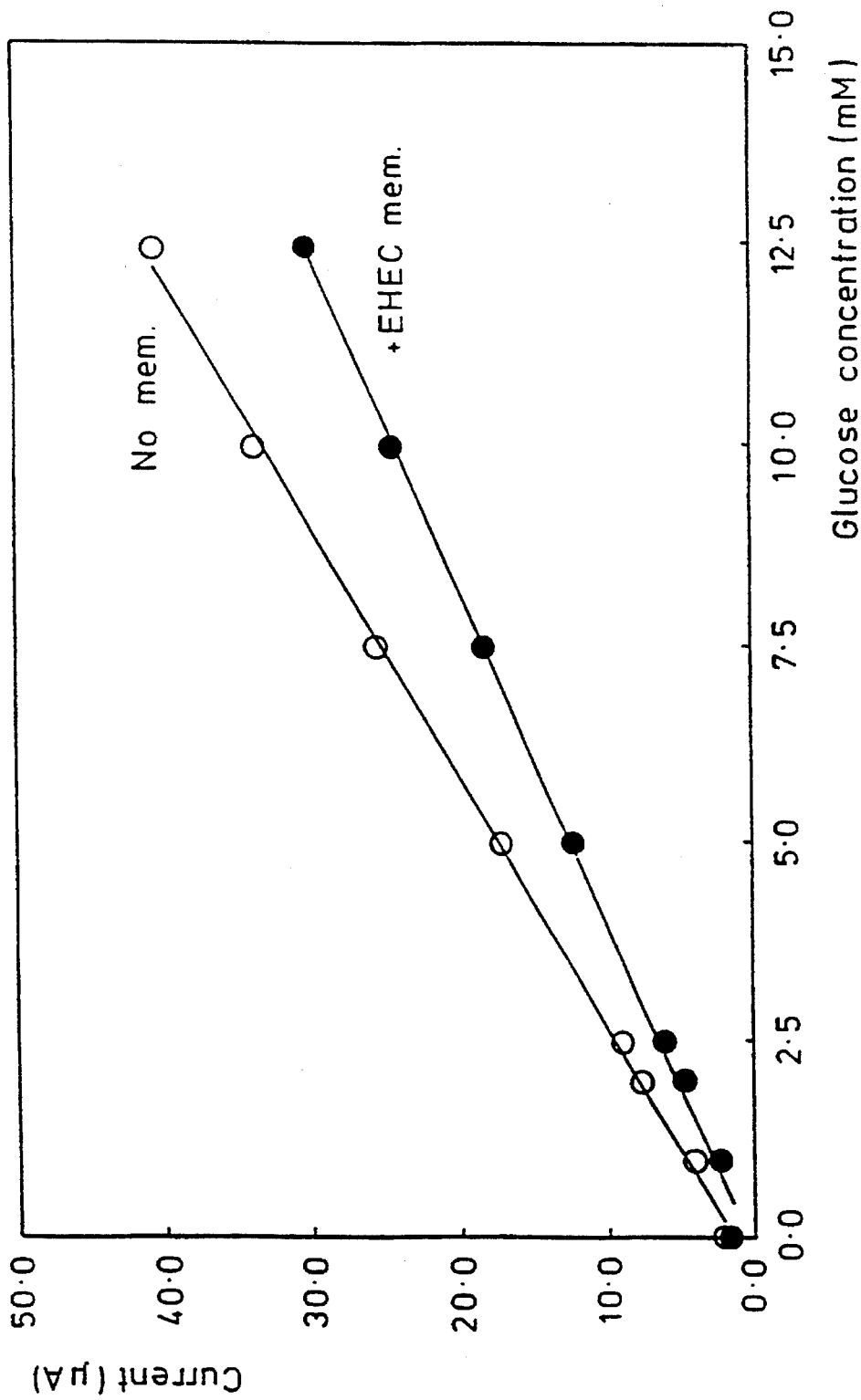
FIGS. 4 to 7 illustrate calibration curves and repeat test results for the electrodes.
Figure 5:
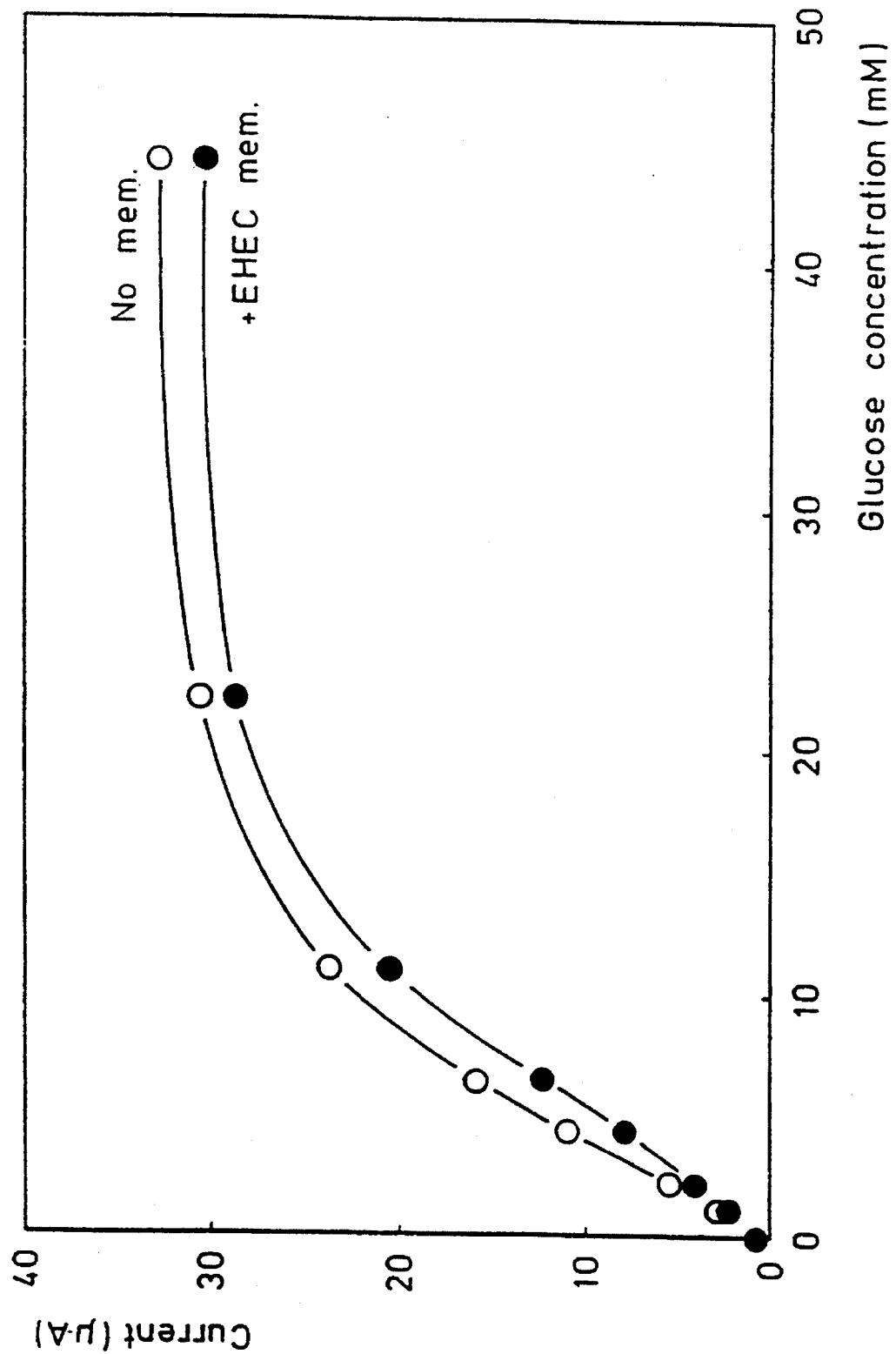
Figure 6:
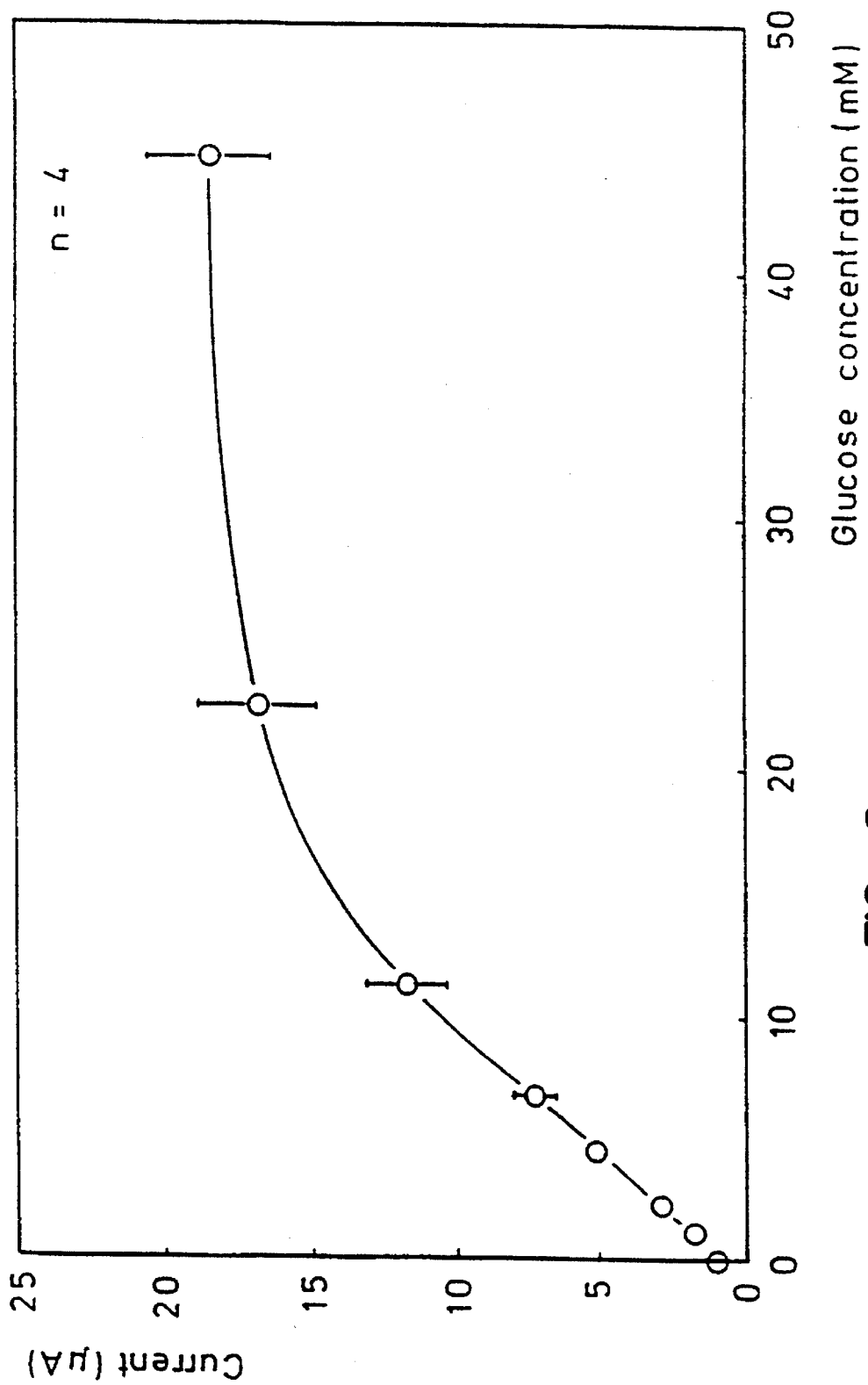
Figure 7:
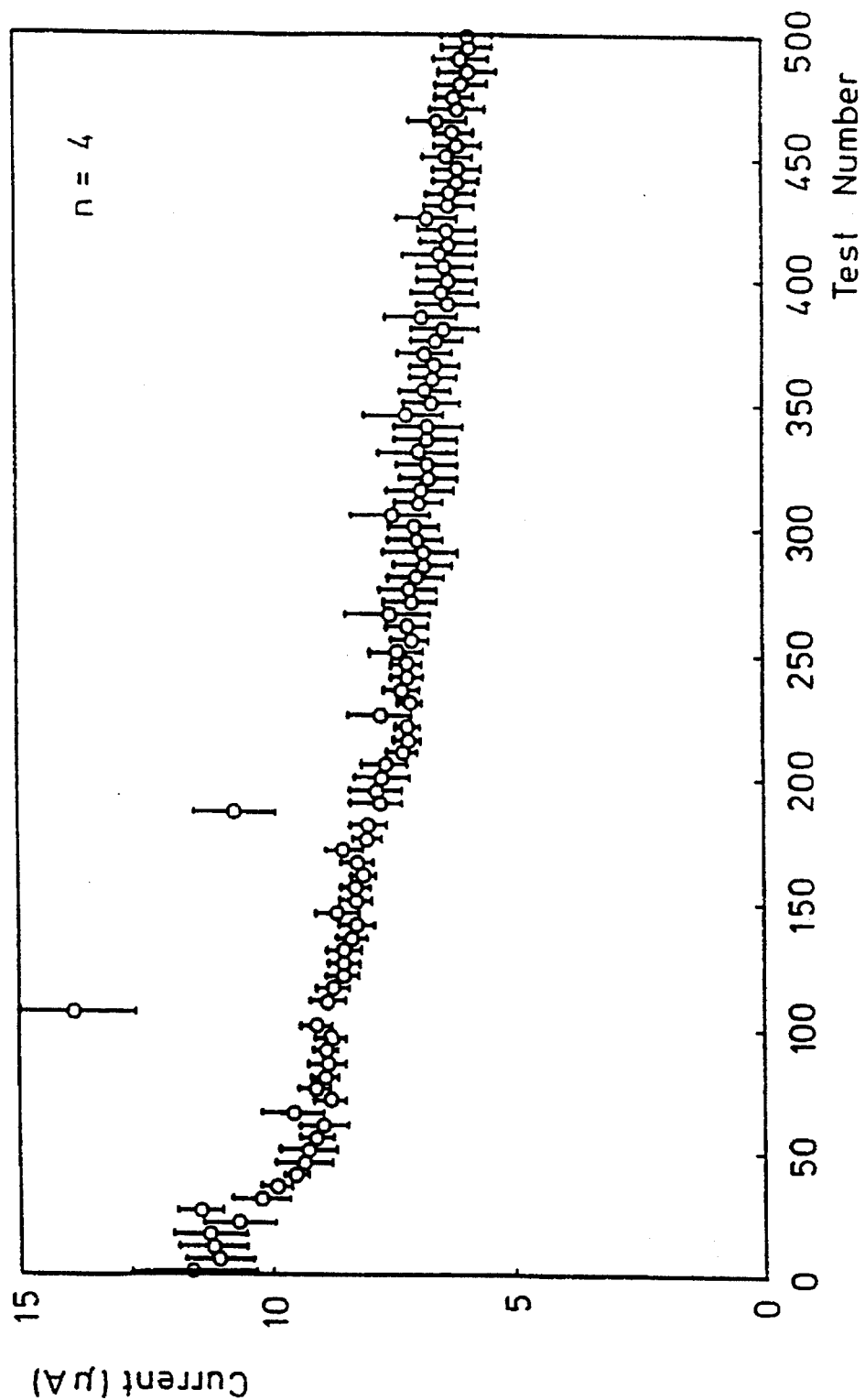
Figure 8:
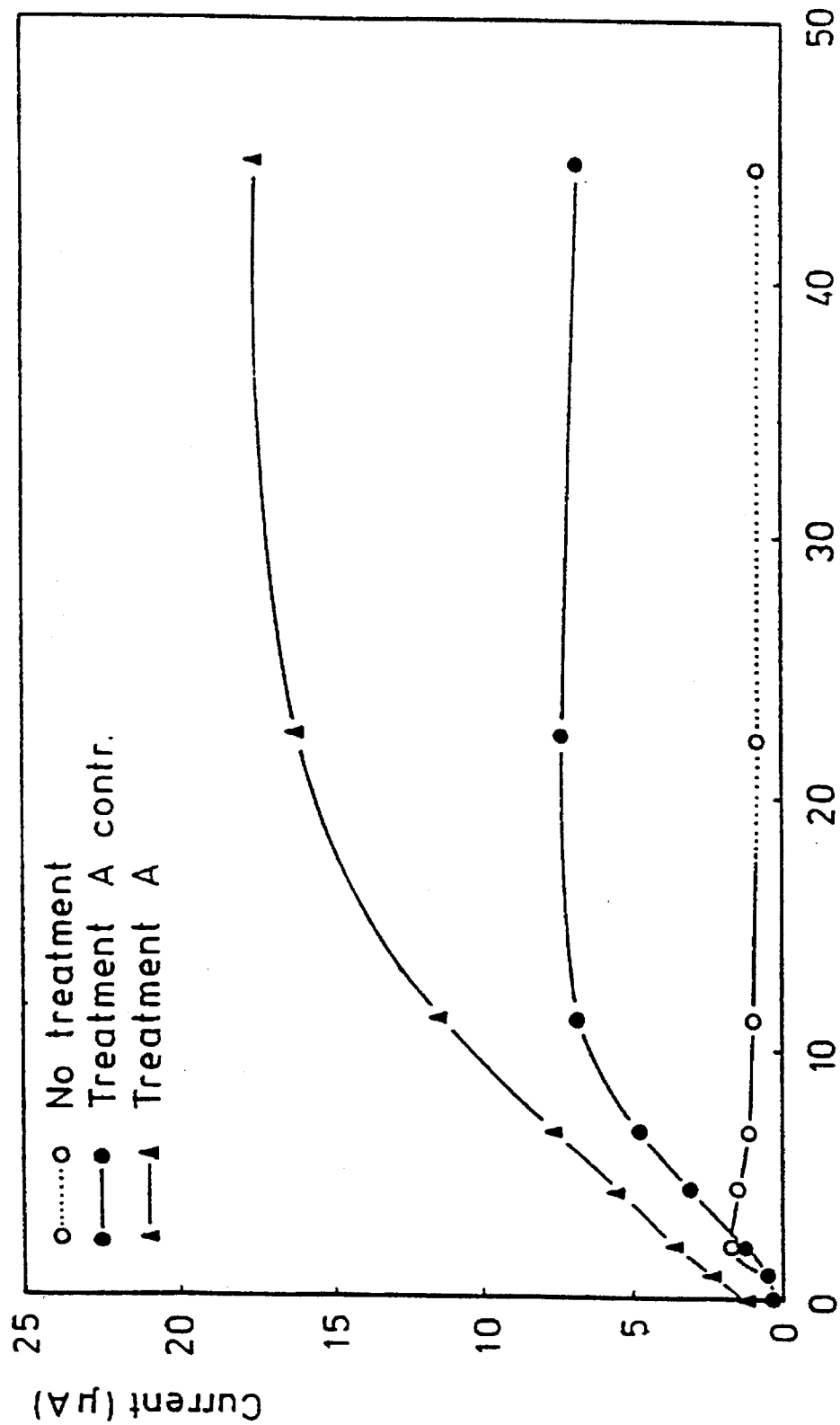
FIGS. 8–10 illustrate calibration curves and repeat test results for the electrodes of Example 3.

Simple treatment with an EHEC membrane with no extra TTF present failed to show the same degree of stability (FIG. 3) and in the calibration curves (FIGS. 4 and 5) the zero glucose value was not high as for the TTR-loaded membrane-coated electrodes.

EXAMPLE 2

Standard TTF/GOD printed electrodes (HEC binder; se previous description of base sensor) were modified by spin-coating with a 6% (w/w) solution of EHEC (ethylhydroxyethyl cellulose) in toluene containing 10 mg g$^{-1}$ TTF. The spin-coating was caried out at approx 1000 rpm at slow speed for five seconds. The membrane coated electrodes were dried rapidly (two to five seconds) in a stream of air followed by storage in a vacuum at room temperature in the presence of silica gel desiccant for up to two days prior to use.

Repeat tests for stability characterisation were made in 6.67 mM glucose in 20 mM sodium phosphate, pH 7.40 containing 100 mM potassium chloride. The tests were of thirty seconds duration at a potential o 200 mV v. Ag/AgCl (printed) at 25° C. in unstirred solution.

The electrodes retained over fifty percent of their initial activity after 500 tests in aqueous 6.67 mM glucose. A calibration curve after 500 samples demonstrated that the electrodes also retained sensitivity to glucose in the range zero to 44 mM.

EXAMPLE 3

Printed electrodes were prepared using DMF as the mediator instead of TTF. It was included in the same quantities using the same technique as for TTF (see experimental procedures).

[(i)+(ii)=Treatment A for DMF].

(i) The membrane was formulated as follows:

10 mg DMF was weighed into a scintillation vial insert and 1 g of six percent (w/w) EHEC in toluene was added. The vial was slowly rotated so as to dissolve the DMF by spin coating.

(ii) The membrane was applied at approx 1000 rpm for two seconds.

(iii) Electrodes were tested as three duplicate pairs-ie. No treatment. Treatment A control (EHEC only) and Treatment A.

The following results were observed:

(i) Untreated DMF/GOD electrodes appeared to fall apart on repeated testing and, therefore, failed to yield a calibration.

(ii) Treatment A control-EHEC (six percent (w/w)) alone appeared to hold the sensor WE together-sufficiently so as to allow calibration and repeated testing.

(iii) Treatment A produced electrodes with stable responses for over 100 tests in buffered glucose (6.67 mM. pH 7.40, 25° C.) with approximately ninety percent of maximal activity remaining. The control electrodes, however, had only sixty percent activity remaining after 100 tests.

(iv) The calibration curve of electrodes modified by treatment A had lost fifty percent sensitivity but retained the same profile throughout the glucose concentration range. The control electrodes, however, had lost more than ninety percent activity and saturated above 10 mM glucose.

The EHEC membrane appeared to:

a. reduce the DMF loss; and b. hold the physical structure together.

The EHEC/DMF layer conferred increased stability on the electrode by providing a reservoir of DMF.

Figure 11:
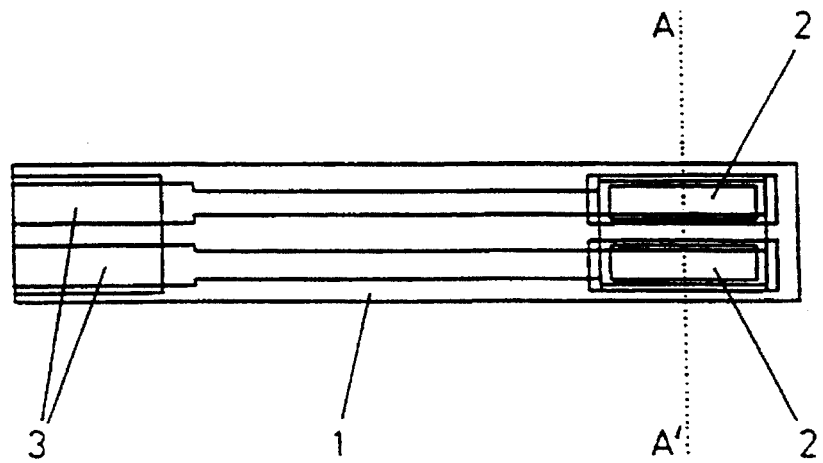
FIGS. 11–12 illustrate plan and sectional views of a preferred spin or dip coated electrode in accordance with this invention.
Figure 12:
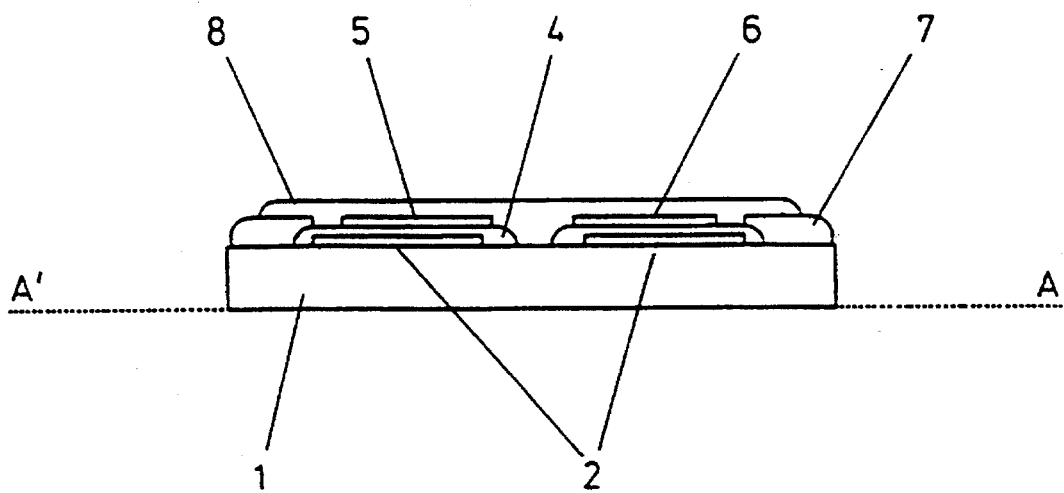

The printed strip electrode shown in FIGS. 11 and 12 comprises a PVC laminar substrate 1(11) carries conductors 2(12) connected to contact 3(13) in the conventional manner. Carbon pads 4(14) overlie the conductors 2(12) and are surmounted by working electrode and reference electrode pads 5(15), 6(16) respectively. Insulation layers 7(17) seal the edges of the electrode and mediator loaded membrane 8(18) is applied over the electrodes 5(15), 6(16).

Figure 13:
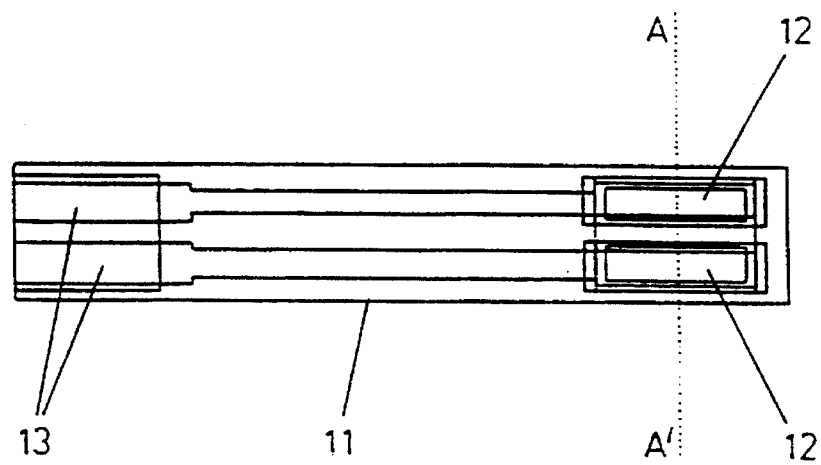
FIGS. 13–14 illustrate plan and sectional views of a second preferred electrode.
Figure 14:
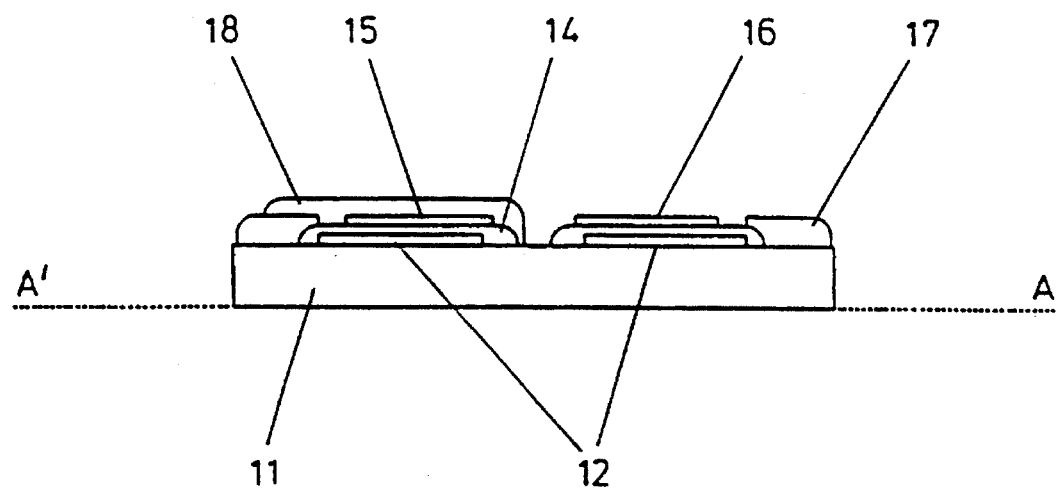

FIGS. 13 and 14 show an alternative embodiment of the invention wherein the mediator containing membrane is applied to a selected area of the biosensor by ink jet printing. The arrangement is generally similar to that described with reference to FIGS. 11 and 12 with the exception that the mediator containing membrane layer 18 is applied to overlie the working electrode 15, leaving the remainder of the biosensor uncoated. This results in economical use of materials and allows subsequent processing steps to be performed on the reference electrode or elsewhere on the biosensor. Automated manufacturing is facilitated.

I claim:

1. An electrochemical biosensor comprising:

a conductive support member:

an enzyme system including a first mediator immobilized on the support member; and a covering membrane incorporating a quantity of a second mediator and covering the enzyme system.

2. A biosensor as claimed in claim 1, wherein the first mediator included in the enzyme system is the same as the second mediator incorporated in the membrane.

3. A biosensor as claimed in claim 1, wherein the second mediator is soluble in a non aqueous solvent.

4. A biosensor as claimed in claim 1 wherein the second mediator is selected from the group consisting of heterofulvalene Pi-donors, metallocenes, quinones, and metal complexes based on platinum group or transition group elements and organic liqands.

5. A biosensor as claimed in claim 1 wherein the membrane comprises a material selected from the group consisting of ethyl hydroxyethyl cellulose, ethyl cellulose, cellulose acetate, polyvinyl chloride, polyurethane, polycarbonate, cellulose nitrate and functionalised aryl polyethers.

6. A biosensor as claimed in claim 1 wherein the second mediator in the membrane is present in a concentration of 5 to 50 mg.g$^{-1}$.

7. A biosensor as claimed in claim 6, wherein the concentration is 5 to 20 mg.g$^{-1}$.

8. A biosensor comprising:

a conductive support member;

an enzyme system including a first mediator immobilised on the support member; and a covering membrane incorporating a quantity of a second mediator and covering the enzyme system;

wherein the biosensor provides a substantially quantitative amperometric response when used for 50 repeat tests with an analyte.

9. A biosensor as claimed in claim 8, wherein said first mediator and said second mediator are identical.

* * * * *

UNITED STATES PATENT AND TRADEMARK OFFICE
CERTIFICATE OF CORRECTION

PATENT NO. : 5,525,511

DATED : June 11, 1996

INVENTOR(S) : D'Costa

It is certified that error appears in the above-indentified patent and that said Letters Patent is hereby corrected as shown below:

ON THE TITLE PAGE:

Item [30] Foreign Application Priority Data "9019126" should read --9019126.3--

Col. 3, line 12 "electrod" should read --electrode--

Col. 4, line 46 "10mg $g^{-1}$" should read --10mg.$g^{-1}$--

Col. 5, line 4 insert --as-- after the word "not"

Col. 5, line 8 "se" should read --see--; line 11 "10mg $g^{-1}$" should read --10mg.$g^{-1}$--; line 20 "o" should read --of--

Col. 6, line 7 delete "(11)" after the numeral --1--; line 8 delete "(12)" after the numeral --2--; line 8 delete "(13)" after the numeral --3--; line 9 delete "(12)" after the numeral --2--; line 9 delete "(14)" after the numeral --4--; line 11 delete "(15)" after the numeral --5--; line 11 delete "(16)" after the numeral --6--; line 11 delete "(17)" after the numeral --7--; line 13 delete "(15)" after the numeral --5--

UNITED STATES PATENT AND TRADEMARK OFFICE
CERTIFICATE OF CORRECTION

PATENT NO. : 5,525,511

DATED : June 11, 1996

INVENTOR(S) : D'Costa

It is certified that error appears in the above-indentified patent and that said Letters Patent is hereby corrected as shown below:

Col. 6, line 13 delete "(16)" after the numeral --6--; line 13 delete "(18)" after the numeral --8--; line 18 "11 and 12" should read --13 and 14--; line 43 "liqands" should read --ligands--

Signed and Sealed this

Seventh Day of October, 1997

Attest:

Attesting Officer

BRUCE LEHMAN

Commissioner of Patents and Trademarks